United States Patent [19]

Ledesma

[11] Patent Number: 4,579,111

[45] Date of Patent: Apr. 1, 1986

[54] LUMBAR LAMENECTOMY PAD

[76] Inventor: Joe C. Ledesma, 431 Elmwood St., Salinas, Calif. 93906

[21] Appl. No.: 576,462

[22] Filed: Feb. 2, 1984

[51] Int. Cl.[4] .............................................. A61F 13/00

[52] U.S. Cl. ........................... 128/134; 128/DIG. 15; 5/431; 269/328

[58] Field of Search ....... 128/134, 133, 135, DIG. 15; 5/431, 61, 81 R, 436, 446; 269/328

[56] References Cited

U.S. PATENT DOCUMENTS

| | | | |
|---|---|---|---|
| 264,678 | 9/1882 | Farrar | 128/135 |
| 2,215,454 | 9/1940 | Condit | 128/134 |
| 3,811,140 | 5/1974 | Burpo | 5/431 |
| 3,924,282 | 12/1975 | Bond | 5/431 |
| 4,210,317 | 7/1980 | Spann et al. | 5/431 |
| 4,321,890 | 3/1982 | Lange et al. | 128/133 |
| 4,506,396 | 3/1985 | Ritchie et al. | 5/431 |

*Primary Examiner*—Gene Mancene
*Assistant Examiner*—John G. Weiss
*Attorney, Agent, or Firm*—Richard L. Miller

[57] ABSTRACT

A support pad is provided so that a patient may be placed on an operating a table in the prone position and provided for ease in breathing and accessibility to the patient's back and lumbar area. Since this is particularly necessary to perform an operation known and a lumbar lamenectomy the current invention is herein called a "lumbar lamenectomy pad". Provision is also made to support the head to ease the air passage and to restrain the arms so as to further immobilize the patient.

7 Claims, 3 Drawing Figures

LUMBAR LAMENECTOMY PAD

BACKGROUND OF THE INVENTION

The present invention relates in general to systems for supporting a patient on an operating table while undergoing surgery. It is necessary during surgery to keep the patient relatively immobile, however, this presents a problem while the patient is lying on his stomach in a prone position as there is a tendency for the patient to roll to one side or the other. The method generally used consists of rolling two blankets, one to be wedged under each side of the patient. This blanket may shift in position and require re-rolling and repositioning. Also, this arrangement places a great deal of weight on the chest making inspiration and exhalation difficult.

An anti-rolling cushion has been described by Sorrell (U.S. Pat. No. 2,724,133) 1953, however Sorrell's cushion does not distribute an individual's weight in such manner as to allow ease of inspiration and exhalation since the individual's chest bears most of the body weight.

SUMMARY OF THE INVENTION

It is therefore the primary object of the present invention to provide a pad to support a patient who is laying in a prone position upon an operating table in such a manner as to prevent him from rolling while allowing the individual to inhale and exhale with ease.

This will facilitate a number of operations, including lumbar lamenectomies. Therefore the present invention is described as a "lumbar lamenectomy pad."

To this end, the present invention is provided with two pyramidal bolsters, triangular in cross section, which rest upon a base cushion, which in turn rests upon the operating table. The triangular cross sectional shape distributes the patients weight so that the patient's sides and shoulders bear most of the weight thereby allowing for ease in inspiration and exhalation.

A further object is to provide head support so as to elevate the head and ease the air passage. To this end a cushioned head rest is provided.

Another object is to provide arm restraints so as to further prevent any rolling or gross movement. To this end arm restraints have been provided along with hook and loop pile type fasteners.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWINGS FIGURES

The figures in the drawings are briefly described as follows.

DETAILED DESCRIPTION OF THE PREFERRED EMBODIMENTS

Figure 1:
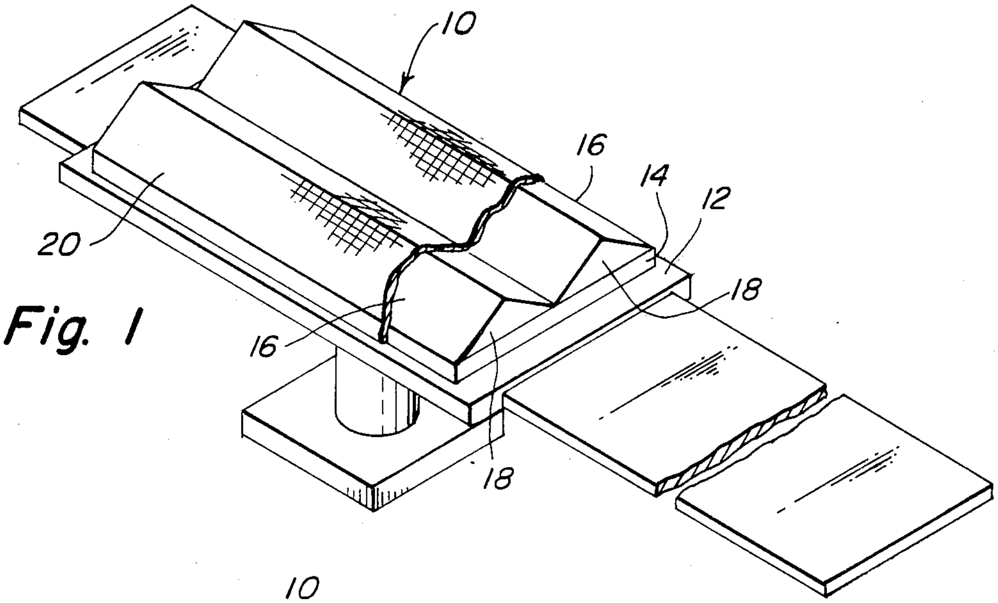
FIG. 1 is a perspective view with parts broken away of the invention showing the invention installed upon an operating table.

The present invention, herein described as a "lumbar lamenectomy pad" is represented by numeral 10 in FIG. 1. The lumbar lamenectomy pad 10 rests upon operating table 12 when a patient is to placed on the operating table in a prone position.

The lumbar lamenectomy pad 10 consists of a base cushion 14 surmounted by two pyramidal shaped bolsters 16 with triangular cross sectional areas represented by numerals 18. The base cushion and bolsters are covered by an upholstery 20. The base cushion is rectangular in shape so as to conform to the dimensions of the fixed working surface of the operating table. The bolsters are dimensioned so as to occupy the entire surface of the base cushion.

Figure 2:
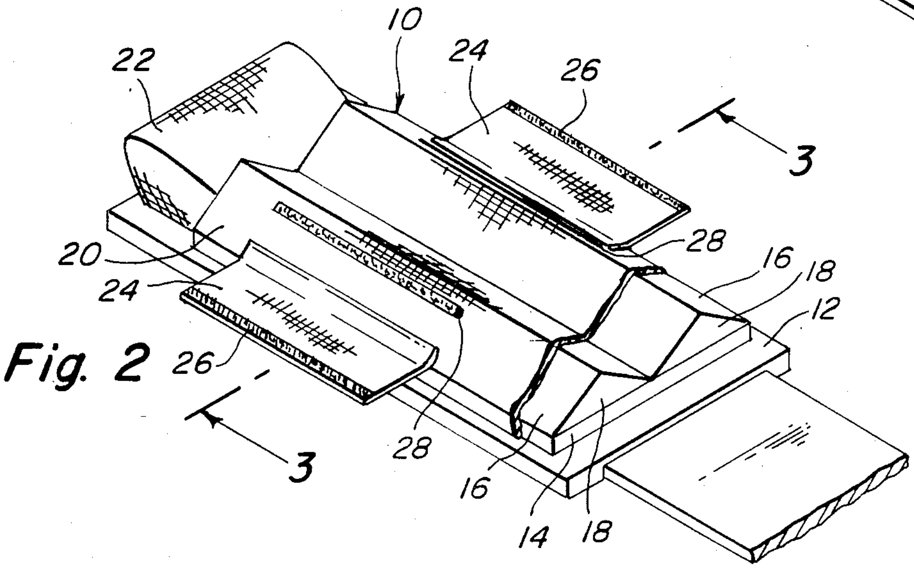
FIG. 2 is a perspective view with parts broken way of a modification of the invention showing the invention installed upon an operating table.
Figure 3:
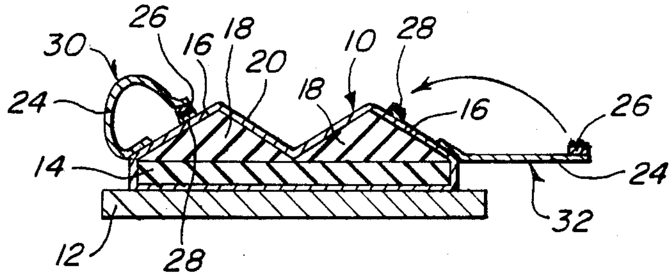
FIG. 3 is a cross sectional view taken on line 3—3 in FIG. 2.

FIG. 2 shows modifications of the invention. A head rest 22 has been added to ease the air passage upon inspiration and exhalation. Arm restraints have been attached to the outsides of the bolsters each comprising a rectangular piece of flexible material 24 and a strip of hook and loop pile fastener material 26 running lengthwise along the free unattached side of the flexible material. The mating piece of hook and loop pile fastener material 28 is attached to the outer surface of each pyramidal bolster 16 so that the flexible material 24 may encircle the patient's arm and so that the flexible material may adhere to the bolster at the line of attachment where the hook and loop pile fasteners meet. FIG. 3 represents a cross sectional view of the modified invention taken along line 3—3 in FIG. 2 and shows the aforementioned arm encirclement as numeral 30 and before encirclement as numeral 32.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A support system for a reclining individual lying prone on his stomach comprising in combination:

a base cushion two bolsters attached to said base cushion, said two bolsters being individually shaped as rectangular pyramids whose end cross section is a triangle and whose base rests upon said cushion, the dimensions of each of said two bolsters being such that the length of each bolster is equal to the length of said base cushion and the width of each said bolster at its base is equal to one half the width of said base pad whereby there is no space between the two bolsters; means for supporting a multiplicity of said individual's limbs and appendages; and means for preventing an individual from rolling while laying in the prone position on the stomach while allowing for expansion and compression of the chest cavity and simultaneously providing access to said individual's entire back and lumbar region.

2. A support system, as recited in claim 1, wherein said base cushion consists of a resilient material formed in a rectangular shape.

3. A support system, as recited in claim 1, wherein means for supporting a multiplicity of said individual's limbs and appendages comprise a head rest and a multiplicity of restraints.

4. A support system, as recited in claim 3, wherein said multiplicity of restraints comprise two arm restraints mounted to opposite sides of said bolsters.

5. A support system, as recite in claim 3, wherein each of said arm restraints comprises a rectangular piece of flexible material for encircling said individual's arm and means for fastening loose end of said material firmly yet removably.

6. A support system, as recited in claim 5, wherein said means for fastening comprise a hook and loop pile fastener attached to the free end of said piece of flexible material and mating hook and loop pile fastener attached to the sloping side wall of said bolster.

7. A support system as recited in claim 1, further comprising upholstery which covers said bolsters and said base cushion.

* * * * *